United States Patent
Mao et al.

(10) Patent No.: US 11,344,672 B2
(45) Date of Patent: May 31, 2022

(54) FILTER DEVICE AND FILTERING INFUSION CONTAINER COMPRISING SAME

(71) Applicant: Gemtier Medical (Jiangsu) Inc., Jiangsu (CN)

(72) Inventors: Chunyuan Mao, Jiangsu (CN); Yaling Mao, Jiangsu (CN)

(73) Assignee: Gemtier Medical (Jiangsu) Inc., Jiangsu (CN)

( * ) Notice: Subject to any disclaimer, the term of this patent is extended or adjusted under 35 U.S.C. 154(b) by 158 days.

(21) Appl. No.: 16/632,089

(22) PCT Filed: Jul. 12, 2018

(86) PCT No.: PCT/CN2018/095363
§ 371 (c)(1),
(2) Date: Jan. 17, 2020

(87) PCT Pub. No.: WO2019/015523
PCT Pub. Date: Jan. 24, 2019

(65) Prior Publication Data
US 2021/0170098 A1 Jun. 10, 2021

(30) Foreign Application Priority Data

Jul. 20, 2017 (CN) .......................... 201710595779.X
Jul. 20, 2017 (CN) .......................... 201720896157.6

(51) Int. Cl.
*A61M 5/165* (2006.01)
*A61J 1/14* (2006.01)
(Continued)

(52) U.S. Cl.
CPC ................ *A61M 5/165* (2013.01); *A61J 1/10* (2013.01); *A61J 1/1456* (2015.05);
(Continued)

(58) Field of Classification Search
CPC ................ A61M 5/165; A61M 5/1411; A61M 2005/1657; A61M 2205/75
See application file for complete search history.

(56) References Cited

U.S. PATENT DOCUMENTS 3,650,093 A * 3/1972 Rosenberg ............ A61M 5/165
96/219
4,162,220 A 7/1979 Servas
(Continued)

FOREIGN PATENT DOCUMENTS

CA 2759518 A1 10/2010
CN 201194918 Y 2/2009
(Continued)

OTHER PUBLICATIONS

First Office Action of Australian patent application 2018302984 dated Nov. 27, 2020.
(Continued)

*Primary Examiner* — Jenna Zhang
(74) *Attorney, Agent, or Firm* — Dinsmore & Shohl LLP

(57) ABSTRACT

A filter device includes a first component having an outer casing with a first accommodating cavity; a second component having a flow channel, an actuator for closing or opening the channel, an actuator head rotatably connected to the second component, an actuator rod inserted in the flow channel, and covered by a seal cover; a filter membrane sandwiched between the first and second components; and a flow path sequentially passing through the channel, the filter membrane, and the first accommodating cavity. A filtering infusion container includes an infusion container and the filter device connected thereto. One end of the flow path leads to the infusion container and the other end leads to the filter membrane. The filter membrane and an infusion fluid are always located in different closed spaces before usage, to
(Continued)

maintain the best integrity of the filter membrane and there is no fluid leakage or actuator loosening.

14 Claims, 3 Drawing Sheets

(51) Int. Cl.
*A61J 1/10* (2006.01)
*A61M 5/14* (2006.01)

(52) U.S. Cl.
CPC ... *A61M 5/1411* (2013.01); *A61M 2005/1657* (2013.01); *A61M 2205/75* (2013.01)

(56) References Cited

U.S. PATENT DOCUMENTS

| | | | |
|---|---|---|---|
| 4,269,222 A | * | 5/1981 | Palti ................ A61M 5/1411 137/433 |
| 4,997,430 A | | 3/1991 | Van der Heiden et al. |
| 2004/0267228 A1 | | 12/2004 | Hattori et al. |
| 2018/0071510 A1 | | 3/2018 | Kunschak |

FOREIGN PATENT DOCUMENTS

| | | | |
|---|---|---|---|
| CN | 203107894 U | | 8/2013 |
| CN | 203355048 U | | 12/2013 |
| CN | 203802874 U | | 9/2014 |
| CN | 104998318 A | | 10/2015 |
| CN | 204745164 U | | 11/2015 |
| CN | 205322919 U | | 6/2016 |
| CN | 105903105 A | | 8/2016 |
| CN | 106237443 A | | 12/2016 |
| CN | 106237443 A | * | 12/2016 |
| CN | 205814865 U | | 12/2016 |
| CN | 205867223 U | * | 1/2017 |
| CN | 205867223 U | | 1/2017 |
| GB | 2122101 A | | 1/1984 |
| JP | S591969 U | | 1/1984 |
| JP | 2015084803 A | | 5/2015 |
| KR | 20130136704 A | | 12/2013 |
| KR | 200471678 Y1 | | 3/2014 |
| KR | 200471678 Y1 | * | 3/2014 |
| WO | 2015160823 A1 | | 10/2015 |
| WO | 2017113904 A1 | | 7/2017 |
| WO | 2018219182 A1 | | 12/2018 |

OTHER PUBLICATIONS

Notice of Rejection of Iranian application 139850140003009745 dated Oct. 30, 2020.
Feb. 2, 2021 Japanese First Office Action issued in Japanese Patent Application No. 2020-524665.
Mar. 16, 2021 European Search Report issued in European Patent Application No. 18835193.6.
Mar. 26, 2021 Indian First Office Action issued in Indian Patent Application No. 202047003736.
First Office Action dated Apr. 16, 2021 of corresponding Canadian Patent Application 3,070,007.
First Office Action dated Mar. 26, 2021 of corresponding Eurasian Patent Application 202090055.
Zhou, R. et al. "Comprehensive Improvement Design of Disposable Infusion Device", Nursing Research, vol. 25, Issue 4, 2011, pp. 1119.
International Search Report and Written Opinion of PCT/CN2018/095363 dated Sep. 13, 2018.
Second Office Action dated Nov. 5, 2021 issued in Canadian Patent Application No. 3,070,007.
June 30th Second Office Action issued in Japanese Application No. 2020-524665.
First Office Action dated Feb. 7, 2022 issued in Korean Patent Application No. 10-2020-7003917.

* cited by examiner

FILTER DEVICE AND FILTERING INFUSION CONTAINER COMPRISING SAME

CROSS-REFERENCE TO RELATED APPLICATIONS

This application is the U.S. national stage of PCT/CN2018/095363 filed Jul. 12, 2018, which claims the priority of Chinese patent application No. 201710595779.X and Chinese patent application No. 201720896157.6, both filed on Jul. 20, 2017, the contents of which are incorporated herein by its entirety.

FIELD OF THE INVENTION

The present invention relates to a filter device and a filtering infusion container comprising same.

BACKGROUND OF THE INVENTION

During the clinical infusion, before using the filter device with the filter membrane, in order to achieve a best filtration effect, a filter membrane should maintain an integrity, which means that the filter membrane should not only be in an unbroken condition, but also demand a first contact with the infusion liquid when used by the patient. However, in the prior art, since the filter membrane has been readily in contact with the vapor and other substances due to a pre-treated different specific sterilization processes (sterilization methods such as steam sterilization and so on in the pharmaceutical industry) in the factory, the expected filtration effect of the filter membrane will be changed and the effectiveness of the filter membrane will also be reduced.

SUMMARY OF THE INVENTION

The technical problem to be solved by the present invention is to overcome the defects in the prior art that the vapor and other substances has been in contact with the filter membrane before the filter membrane is used by the patient, and thus the expected filtration effect of the filter membrane has been changed and the effectiveness of the filter membrane has been reduced, and the present application thereby provides a filter device and a filtering infusion container comprising same.

The present invention solves the technical problem mentioned above by the following technical solutions:

A filter device, characterized in that the filter device comprises:

A first component comprising an outer casing, wherein a first side wall and a bottom wall of the outer casing are surrounded to form a first accommodating cavity;

A second component connected to first component, wherein the second component comprises a flow channel;

An actuator used to close or open the flow channel, wherein the actuator comprises a head portion and a rod portion which are connected with each other, wherein the head portion of the actuator is rotatably connected to the second component and the rod portion of the actuator is inserted in the flow channel, and wherein the outer surface of the rod portion of the actuator is covered by a seal cover; and A filter membrane sandwiched between the first component and the second component;

Wherein the filter device further comprises a flow path which sequentially passes through the flow channel, the filter membrane and the first accommodating cavity.

In this technical solution, the sealing method of using the seal cover enables the filter device to continually maintain a good impermeability after being implemented by a specific sterilization processes (sterilization methods such as steam sterilization and so on in the pharmaceutical industry), which means that the filter membrane and the infusion fluid are always located in different closed spaces before usage by the patient, so that the best integrity of the filter membrane can be maintained, moreover no fluid leakage will happen in the filter device, and the actuator will not get loose during transportation.

Preferable, central axis of the actuator is perpendicular to central axis of the flow channel, wherein the actuator motions rotationally around the central axis of the actuator while motions linearly in a direction perpendicular to the central axis of the flow channel.

Preferable, the second component further comprises a mount which is provided with an inner cavity, wherein the rod portion of the actuator is inserted in the inner cavity, and central axis of the inner cavity is perpendicular to the central axis of the flow channel.

Preferable, one side of the head portion facing to the flow channel is provided with a limiting slot, and one end of a side wall of the mount facing to the limiting slot is inserted in the limiting slot, wherein the limiting slot and the side wall of the mount are engaged with each other to limit the movement of the actuator.

Preferable, outer surface of the side wall of the mount is provided with a helical protrusion, and inner surface of the limiting slot is provided with a helical groove which is corresponding to the helical protrusion, wherein the helical protrusion and the helical groove are engaged with each other to limit the rotating motion trajectory of the actuator.

In this technical solution, the engagement of the helical protrusion and the helical groove enables the actuator to move more smoothly and controlling the movement speed and the distance of the actuator more steadily that closes or opens the flow channel; meanwhile, the helical protrusion and the helical groove engaged with each other can limit the motions of the actuator under a pressure directly in a direction away from the mount, such that the flow channel can be prevented from being opened.

Preferable, inner wall of the inner cavity is provided with a limiting step which extends in a radial direction towards the central axis of the inner cavity, and outer wall of the rod portion is provided with a limiting protrusion which extends in a radial direction towards the mount, wherein the limiting protrusion abuts against to the limiting step, and wherein the limiting protrusion and the limiting step are engaged with each other to limit the movement of the actuator in the direction away from the mount.

In this technical solution, the limiting protrusion and the limiting step engaged with each other limit the moving position of the actuator and prevents the actuator from falling out of the mount which can ensure the safety.

Preferable, the first component further comprises an inner casing, wherein one end of the inner casing passes through and within the first accommodating cavity, and wherein another end of the inner casing passes though the bottom wall of the outer casing and be located outside of the outer casing, and wherein the bottom wall is hermetically connected to outer surface of the second side wall of the inner casing, and wherein the second side wall and top plate are surrounded to form a second accommodating cavity, and wherein the second side wall which the inner casing passes through and within the first accommodating cavity is provided with a plurality of gaps, and wherein the plurality of gaps are all communicated with the first accommodating cavity and the second accommodating cavity.

Wherein the flow path sequentially passes through the flow channel, the filter membrane, the first accommodating cavity, the gap and the second accommodating cavity.

In this technical solution, by providing the structure of the inner casing, it enables that after the infusion fluid arrives into the first accommodating cavity along the flow path and then the liquid level reaches a specified height, the infusion fluid enters the second accommodating cavity through the gaps, after that, the infusion fluid is discharged downwards, which can prevent the infusion fluid from dripping into the pinhole of the injection bottle pin directly in the form of water droplets after being filtered by the filter membrane and forming continuous air embolism thereby, and thus the infusion process can be better controlled. Meanwhile, by providing the structure of the inner casing, due to the block of the top plate of the inner casing, it can prevent the injection bottle pin from pricking the filter membrane directly when the injection bottle pin is inserted into the second accommodating cavity, and thus the safety in the operating process can be improved. Furthermore, the gap in this technical solution can also prevent the bubbles from entering the second accommodating cavity, and thus the security of the infusion fluid can be ensured.

Preferable, the first component is integrally molded.

Preferable, the second side wall of the inner casing comprises a first section and a second section which are connected with each other, wherein thickness of the first section is less than the one of the second section; wherein the first section is located within the first accommodating cavity and is provided with the plurality of gaps; wherein the second section is located out of the outer casing, and the bottom wall of the outer casing is hermetically connected to the outer surface of the second section adjacent to one end of the first section.

Preferable, the filter device further comprises a sealing component, wherein the sealing component is snapped to other end of the inner casing and is used to seal the second accommodating cavity.

Preferable, the seal cover is screwed with the rod portion.

Preferable, material of the seal cover is rubber.

Preferable, one end of the first section is snapped to the corresponding end of the second section, and the first section and the second section are hermetically connected to each other.

The present invention further provides a filtering infusion container, wherein it comprises the filter device as mentioned above, and wherein the filtering infusion container further comprises an infusion container connected to the filter device, and wherein one end of the flow path is leaded to the infusion container, and the other end is leaded to the filter membrane.

The positive effects of the present invention are:

1. The structure of the present invention is compact, and possesses a high utilization rate of space;

2. By providing the seal cover on the outer surface of the actuator, the present invention enables the filer device to continually maintain a good impermeability after being implemented by a specific sterilization processes (sterilization methods such as steam sterilization and so on in the pharmaceutical industry), which means that the filter membrane and the infusion fluid are always located in different closed spaces before usage by the patient, so that the best integrity of the filter membrane can be maintained, moreover no fluid leakage will happen in the filter device, and the actuator will not get loose during transportation;

3. By providing the helical protrusion and the helical groove engaged with each other, the present invention enables the actuator to move more smoothly and controlling the movement speed and the distance of the actuator more steadily that closes or opens the flow channel; meanwhile, the helical protrusion and the helical groove engaged with each other can limit the motions of the actuator under a pressure directly in a direction away from the mount, such that the flow channel can be prevented from being opened;

4. By providing the helical protrusion and the helical groove engaged with each other, the present invention limits the moving position of the actuator and prevents the actuator from falling out of the mount which ensures the safety;

5. By providing the structure of the inner casing, the present invention not only prevents the infusion fluid from dripping into the pinhole of the injection bottle pin directly in the form of water droplets after being filtered by the filter membrane and forming continuous air embolism thereby, and thus the infusion process can be controlled optimally, but also due to the block of the top plate of the inner casing, it can prevent the injection bottle pin from pricking the filter membrane directly, and thus the safety in the operating process can be improved. Furthermore, the gap of the inner casing can also effect to prevent the bubbles from entering the second accommodating cavity, and thus the security of the infusion fluid can be ensured.

EXPLANATION OF THE REFERENCE NUMBERS

Figure 1:
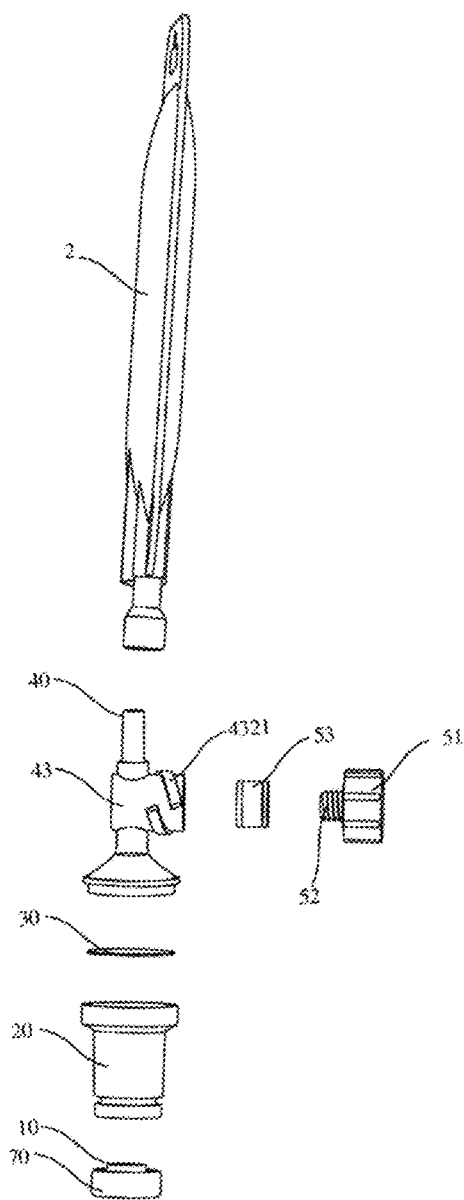
FIG. 1 is an exploded structure view of the filtering infusion container in an optimal embodiment according to the present invention.

Filter device 1
Sealing component 10
First component 20
Outer casing 21
First side wall 211
Bottom wall 212
First accommodating cavity 213
Inner casing 22
Second side wall 221
First section 2211
Second section 2212
Top plate 222
Second accommodating cavity 223
Gap 224
Filter membrane 30
Second component 40
Flow channel 41
Mount 43
Inner cavity 431
Limiting step 4311
Side wall of the mount 432
Helical protrusion 4321

Actuator 50
Head portion 51
Limiting slot 512
Helical groove 513
Rod portion 52
Limiting protrusion 521
Seal cover 53
Flow path 60
Fastener 70
Infusion container 2

DETAILED DESCRIPTION OF THE PREFERRED EMBODIMENT

Hereinafter, the present invention will be described in detail with respect to the embodiment, but is not intended to be limited in the scope disclosed therein.

Figure 2:
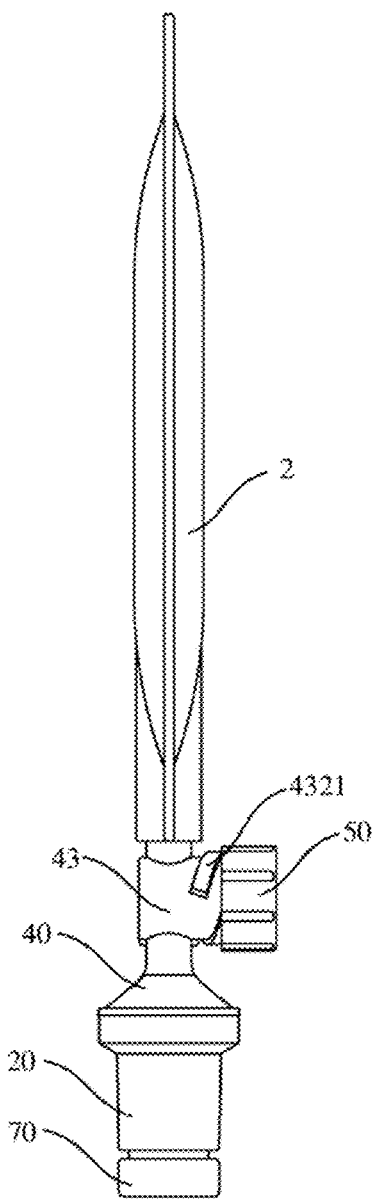
FIG. 2 is a perspective view of the filtering infusion container in an optimal embodiment according to the present invention.
Figure 3:
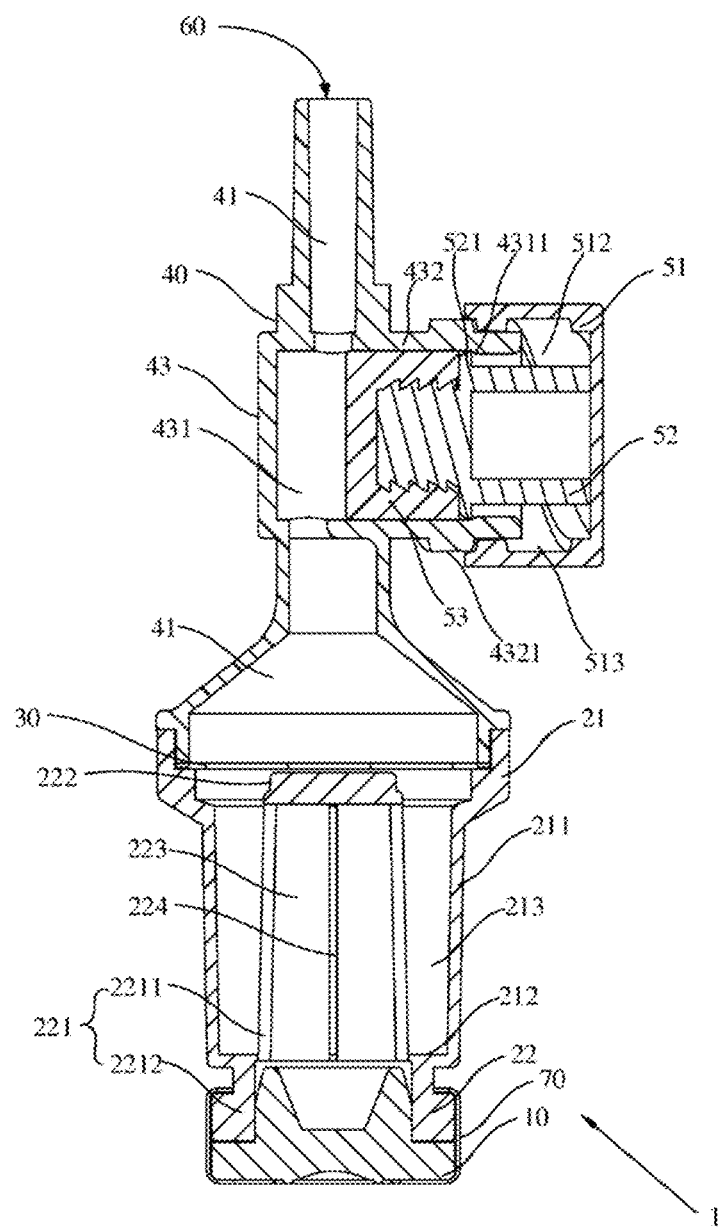
FIG. 3 is a cross-section view of the actuator of the filter device when opening the flow channel in an optimal embodiment according to the present invention.

Referring to FIGS. 1-3, it can be understood that the embodiment of the present invention provides a filter device 1 comprising a sealing component 10, a first component 20, a filter membrane 30, a second component 40 and an actuator 50. One end of the first component 20 is snapped to the corresponding end of the second component 40, and the first component 20 and the second component 40 are hermetically connected with each other. The filter membrane 30 is sandwiched between the first component 20 and the second component 40. The first component 20 is integrally molded.

The first component 20 comprises an outer casing 21 and an inner casing 22. A first side wall 211 and a bottom wall 212 of the outer casing 21 surround to form a first accommodating cavity 213. One end of the inner casing 22 passes through and within the first accommodating cavity 213, and another end of the inner casing 22 passes though the bottom wall 212 of the outer casing 21 and is located outside of the outer casing 21, and the bottom wall 212 is hermetically connected to outer surface of the second side wall 221 of the inner casing 22, and the second side wall 221 and top plate 222 surround to form a second accommodating cavity 223, and the second side wall 221 of the inner casing 22 which passes through and within the first accommodating cavity 213 is provided with four gaps 224, and the four gaps 224 are all communicated with the first accommodating cavity 213 and the second accommodating cavity 223. The four gaps 224 are distributed circumferentially with an isometric interval along the second accommodating cavity 223. In other alternative embodiment, the number of the gaps 224 can also be two, three or other quantities.

The second side wall 221 of the inner casing 22 comprises a first section 2211 and a second section 2212 which are connected with each other, wherein the thickness of the first section 2211 is less than that of the second section 2212; wherein the first section 2211 is located within the first accommodating cavity 213 and is provided with the gaps 224 mentioned above; wherein the second section 2212 is located outside of the outer casing 21, and the bottom wall 212 of the outer casing 21 is hermetically connected to the outer surface of the second section 2212 adjacent to one end of the first section 2211.

The sealing component 10 is snapped to other end of the inner casing 22 and is used to seal the second accommodating cavity 223. The material of the sealing component 10 is rubber. In the present embodiment, the sealing component 10 is covered by a fastener 70, wherein one end of the fastener 70 is circumferentially snapped to the outside of one end of inner casing 22 adjacent to the sealing component 10. The fastener 70 is used to better fix the sealing component 10 to one end of the inner casing 22.

The second component 40 comprises a flow channel 41. The actuator 50 is used to close or open the flow channel 41. The central axis of the actuator 50 is perpendicular to the central axis of the flow channel 41, wherein the actuator 50 motions rotationally around the central axis of the actuator 50 while motions linearly in a direction perpendicular to the central axis of the flow channel 41. The actuator 50 comprises a head portion 51 and a rod portion 52 which are connected with each other, wherein the diameter of the head portion 51 is greater than the one of the rod portion 52. The head portion 51 of the actuator 50 is rotatably connected to the second component 40. The rod portion 52 of the actuator 50 is inserted in the flow channel 41, and the outer surface of the rod portion 52 of the actuator 50 is covered by a seal cover 53. In this way, the sealing method of using the seal cover 53 enables the filter device 1 to continually maintain a good impermeability after being implemented by a specific sterilization processes (sterilization methods such as steam sterilization and so on in the pharmaceutical industry), which means that the filter membrane 30 and the infusion fluid are always located in different closed spaces before usage by the patient, so that the best integrity of the filter membrane 30 can be maintained, in the meantime no liquid leakage will happen in the filter device, and the actuator will not get loosen during transportation. In the present embodiment, the seal cover 53 is screwed with the rod portion 52. The material of the seal cover 53 is rubber.

The second component 40 further comprises a mount 43. The mount 43 is provided with an inner cavity 431, wherein the rod portion 52 of the actuator 50 is inserted in the inner cavity 431, and central axis of the inner cavity 431 is perpendicular to the central axis of the flow channel 41.

One side of the head portion 51 facing to the flow channel 41 is provided with a limiting slot 512, and one end of a side wall 432 of the mount facing to the limiting slot 512 is inserted in the limiting slot 512, wherein the limiting slot 512 and the side wall 432 of the mount are engaged with each other to limit the movement of the actuator 50.

In the present embodiment, the outer surface of the side wall 432 of the mount is provided with a helical protrusion 4321, and the inner surface of the limiting slot 512 is provided with a helical groove 513 which is corresponding to the helical protrusion 4321, wherein the helical protrusion 4321 and the helical groove 513 are engaged with each other to limit the rotating motion trajectory of the actuator 50. In this way, the provision and engagement of the helical protrusion 4321 and the helical groove 513 enables the actuator 50 to move more smoothly and controlling the movement speed and the distance of the actuator 50 more steadily that closes or opens the flow channel; meanwhile, the helical protrusion 4321 and the helical groove 513 engaged with each other can limit the motions of the actuator 50 under a pressure directly in a direction away from the mount 43, such that the flow channel 41 can be prevented from being opened.

Specifically, as for the seal cover 53 of the actuator 50, when the actuator 50 closes the flow channel 41, meanwhile the seal cover 53 keeps in a steam sterilization state, the expanding pressure of the above medicine liquid due to the rising temperature will apportion on the whole seal cover 53. At this time, since the seal cover 53 effects to seal the flow channel 41, a dead space (which means the air will be unable to be discharged normally) with certain volume will form at the terminal end of the flow channel 41. Similarly, during in a steam sterilization state, since the rising temperature (the steam sterilization temperature reaches 121° C.) will lead to the air in the dead space being expanded, the actuator 50 will be pushed to motion in a direction away from the mount 43, which is motioning in a direction of opening the flow channel 41, thus, it will come into a potential risk that the flow channel 41 will be opened during the sterilization and the medicine liquid will permeate the filter membrane resulting in an invalidation thereof. While, the screw engagement between the helical groove 513 of the actuator and the helical protrusion 4321 of the mount can neutralize the expanding force from the air, and thus the filter membrane will be prevented from being wet during the sterilization.

The inner wall of the inner cavity 431 of the mount is provided with a limiting step 4311 which extends in a radial direction towards the central axis of the inner cavity 431, and outer wall of the rod portion 52 is provided with a limiting protrusion 521 which extends in a radial direction towards the mount 43, wherein the limiting protrusion 521 abuts against to the limiting step 4311, and wherein the limiting protrusion 521 and the limiting step 4311 are engaged with each other to limit the movement of the actuator 50 in the direction away from the mount 43. In this way, the provision and engagement of the limiting protrusion 521 and the limiting step 4311 limits the moving position of the actuator 50 and prevents the actuator 50 from falling out of the mount 43, which ensures the safety.

The filter device 1 further comprises a flow path 60 which sequentially passes through the flow channel 41, the filter membrane 30, the first accommodating cavity 213, the gap 224 and the second accommodating cavity 223.

The operating principle of the present invention is that: when the infusion fluid arrives in the first accommodating cavity along the flow path, the liquid level of the infusion fluid rises gradually, after the liquid level reaches the specified height, the infusion fluid enters the second accommodating cavity through the gap, and after that, the infusion fluid is discharged downwards, which can prevent the infusion fluid from dripping into the pinhole of the injection bottle pin directly in the form of water droplets after being filtered by the filter membrane and forming continuous air embolism thereby, and thus the infusion process can be better controlled. Meanwhile, by providing the structure of the inner casing, due to the block of the top plate of the inner casing, it can prevent the injection bottle pin from pricking the filter membrane directly when the injection bottle pin is inserted into the second accommodating cavity, and thus the safety in the operating process can be improved. Furthermore, the gap in this technical solution can also prevent the bubbles from entering the second accommodating cavity, and thus the security of the infusion fluid can be ensured.

The present embodiment further provides a filtering infusion container, wherein it comprises the filter device 1 as mentioned above, and wherein the filtering infusion container further comprises an infusion container 2 connected to the filter device 1, and wherein one end of the flow path 60 is leaded to the infusion container 2, and other end is leaded to the filter membrane 30.

While the foregoing specific embodiment has been described in the present invention, it will be understood by those skilled in the art that those are only for the illustration purposes and the scope sought to be protected by the present invention is limited by the accompanying claims. Those skilled in the art can implement various changes and modifications to these embodiments without departing from the principle and essence of the present invention, however these changes and modifications will all fall into the scope sought to be protected the present invention.

What is claimed is:

1. A filter device, comprising:
    a first component comprising an outer casing, wherein a first side wall and a bottom wall of the outer casing surround to form a first accommodating cavity;
    a second component connected to the first component, wherein the second component comprises a flow channel;
    an actuator used to close or open the flow channel, wherein the actuator comprises a head portion and a rod portion which are connected with each other, wherein the head portion of the actuator is rotatably connected to the second component and the rod portion of the actuator is inserted in the flow channel, and wherein an outer surface of the rod portion of the actuator is covered by a seal cover; and
    a filter membrane sandwiched between the first component and the second component;
    wherein;
        the first component further comprises an inner casing, one end of the inner casing passing through and within the first accommodating cavity, and an other end of the inner casing passing though the bottom wall of the outer casing and located outside of the outer casing;
        the bottom wall of the first component is hermetically connected to an outer surface of a second side wall of the inner casing;
        the second side wall of the inner casing and a top plate of the inner casing surround to form a second accommodating cavity;
        the second side wall of the inner casing which passes through and within the first accommodating cavity is provided with a plurality of gaps, the plurality of gaps providing fluid communication between the first accommodating cavity and the second accommodating cavity;
        the top plate is disposed between the filter membrane and the second accommodating cavity; and
        a flow path is defined as sequentially passing through the flow channel, the filter membrane, the first accommodating cavity, the plurality of gaps and the second accommodating cavity.

2. The filter device according to claim 1, wherein a central axis of the actuator is perpendicular to a central axis of the flow channel, wherein the actuator is configured to rotate around a central axis of the actuator while moving linearly in a direction perpendicular to the central axis of the flow channel.

3. The filter device according to claim 2, wherein the second component further comprises a mount which is provided with an inner cavity, wherein the rod portion of the actuator is positioned within the inner cavity, and a central axis of the inner cavity is perpendicular to the central axis of the flow channel.

4. The filter device according to claim 3, wherein one side of the head portion facing to the flow channel is provided with a limiting slot, and one end of a side wall of the mount facing to the limiting slot is inserted in the limiting slot, wherein the limiting slot and the side wall of the mount are engaged with each other to limit the movement of the actuator.

5. The filter device according to claim 4, wherein an outer surface of the side wall of the mount is provided with a helical protrusion, and an inner surface of the limiting slot is provided with a helical groove which corresponds to to the helical protrusion, wherein the helical protrusion and the helical groove are engaged with each other to limit a rotating motion trajectory of the actuator around the central axis of the actuator while moving linearly in a direction perpendicular to the central axis of the flow channel.

6. The filter device according to claim 3, wherein an inner wall of the inner cavity is provided with a limiting step which extends in a radial direction towards the central axis of the inner cavity, and an outer wall of the rod portion is provided with a limiting protrusion which extends in a radial direction towards the mount, wherein the limiting protrusion abuts against to the limiting step, and wherein the limiting protrusion and the limiting step are engaged with each other to limit the movement of the actuator in the direction away from the mount.

7. The filter device according to claim 1, wherein the first component is integrally molded.

8. The filter device according to claim 1, wherein the second side wall of the inner casing comprises a first section and a second section which are connected with each other, wherein thickness of the first section is less than that of the second section; wherein the first section is located within the first accommodating cavity and is provided with the plurality of gaps; wherein the second section is located outside of the outer casing, and the bottom wall of the outer casing is hermetically connected to an outer surface of the second section adjacent to one end of the first section.

9. The filter device according to claim 1, wherein the filter device further comprises a sealing component, wherein the sealing component is snapped to the other end of the inner casing and is used to seal the second accommodating cavity.

10. The filter device according to claim 1, wherein the seal cover is screwed with the rod portion.

11. The filter device according to claim 1, wherein material of the seal cover is rubber.

12. The filter device according to claim 1, wherein one end of the first component is snapped to a corresponding end of the second component, and the first component and the second component are hermetically connected to each other.

13. The filter device according to claim 1, wherein the second accommodating cavity is surrounded by the first accommodating cavity.

14. A filtering infusion container, comprising:
the filter device according to claim 1; an infusion container connected to the filter device;
and wherein one end of the flow path leads to the infusion container, and the other end leads to the filter membrane.

* * * * *